(12) United States Patent
Kararli et al.

(10) Patent No.: US 7,695,736 B2
(45) Date of Patent: Apr. 13, 2010

(54) RECONSTITUTABLE PARENTERAL COMPOSITION

(75) Inventors: Tugrul T. Kararli, Skokie, IL (US);
Sandeep Nema, Grayslake, IL (US);
Aziz Karim, Skokie, IL (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/113,281

(22) Filed: Apr. 1, 2002

(65) Prior Publication Data

US 2003/0078266 A1      Apr. 24, 2003

Related U.S. Application Data

(60) Provisional application No. 60/281,058, filed on Apr. 3, 2001.

(51) Int. Cl.
*A61K 9/14*      (2006.01)
(52) U.S. Cl. ..................................... 424/489
(58) Field of Classification Search ............... 424/489; 514/247, 406, 456, 690, 471
See application file for complete search history.

(56) References Cited

U.S. PATENT DOCUMENTS

| | | | |
|---|---|---|---|
| 4,434,163 A | 2/1984 | Lombardino | 424/246 |
| 4,677,195 A * | 6/1987 | Hewick et al. | 514/8 |
| 4,797,388 A * | 1/1989 | Francis | 514/23 |
| 5,036,060 A * | 7/1991 | Alam et al. | 514/110 |
| 5,344,991 A | 9/1994 | Reitz et al. | 568/34 |
| 5,380,738 A | 1/1995 | Norman et al. | 514/374 |
| 5,393,790 A | 2/1995 | Reitz et al. | 514/709 |
| 5,401,765 A | 3/1995 | Lee | 548/406 |
| 5,418,254 A | 5/1995 | Huang et al. | 514/604 |
| 5,420,343 A | 5/1995 | Koszyk et al. | 562/468 |
| 5,434,178 A | 7/1995 | Talley et al. | 514/406 |
| 5,436,265 A | 7/1995 | Black et al. | 514/420 |
| 5,466,823 A | 11/1995 | Talley et al. | 548/377.1 |

(Continued)

FOREIGN PATENT DOCUMENTS

EP      0 799 823      10/1997

(Continued)

OTHER PUBLICATIONS

STN Registry Database, Registry No. 198470-85-8, Entered in Database Dec. 12, 1997, Retrieved from Database Jul. 13, 2005.*

(Continued)

*Primary Examiner*—Eric E. Silverman
(74) *Attorney, Agent, or Firm*—Gregg C. Benson; A. Dean Olson

(57) ABSTRACT

A pharmaceutical composition comprises, in powder form, (a) at least one water-soluble therapeutic agent selected from selective COX-2 inhibitory drugs and prodrugs and salts thereof, for example parecoxib sodium, in a therapeutically effective total amount constituting about 30% to about 90% by weight, (b) a parenterally acceptable buffering agent in an amount of about 5% to about 60% by weight, and optionally (c) other parenterally acceptable excipient ingredients in a total amount not greater than about 10% by weight, of the composition. The composition is reconstitutable in a parenterally acceptable solvent liquid to form an injectable solution. A lyophilization process is provided for preparation of such a composition.

34 Claims, 1 Drawing Sheet

U.S. PATENT DOCUMENTS

| | | | |
|---|---|---|---|
| 5,474,995 A | 12/1995 | Ducharme et al. | 514/241 |
| 5,475,018 A | 12/1995 | Lee et al. | 514/406 |
| 5,486,534 A | 1/1996 | Lee et al. | 514/406 |
| 5,510,368 A | 4/1996 | Lau et al. | 514/419 |
| 5,521,213 A | 5/1996 | Prasit et al. | 514/443 |
| 5,536,752 A | 7/1996 | Ducharme et al. | 514/602 |
| 5,543,297 A | 8/1996 | Cromlish et al. | 435/25 |
| 5,547,975 A | 8/1996 | Talley et al. | 514/406 |
| 5,550,142 A | 8/1996 | Ducharme et al. | 514/365 |
| 5,552,422 A | 9/1996 | Gauthier et al. | 514/368 |
| 5,585,504 A | 12/1996 | Desmond et al. | 549/323 |
| 5,593,992 A | 1/1997 | Adams et al. | 514/235.8 |
| 5,596,008 A | 1/1997 | Lee | 514/347 |
| 5,604,253 A | 2/1997 | Lau et al. | 514/415 |
| 5,604,260 A | 2/1997 | Guay et al. | 514/605 |
| 5,616,458 A | 4/1997 | Lipsky et al. | 435/4 |
| 5,616,601 A | 4/1997 | Khanna et al. | 514/399 |
| 5,620,999 A | 4/1997 | Weier et al. | 514/398 |
| 5,633,272 A | 5/1997 | Talley et al. | 514/378 |
| 5,639,780 A | 6/1997 | Lau et al. | 514/419 |
| 5,643,933 A | 7/1997 | Talley et al. | 514/372 |
| 5,658,903 A | 8/1997 | Adams et al. | 514/235.8 |
| 5,668,161 A | 9/1997 | Talley et al. | 514/365 |
| 5,670,510 A | 9/1997 | Huang et al. | 514/278 |
| 5,677,318 A | 10/1997 | Lau | 514/361 |
| 5,681,842 A | 10/1997 | Dellaria et al. | 514/367 |
| 5,686,460 A | 11/1997 | Nicolaï et al. | 514/277 |
| 5,686,470 A | 11/1997 | Weier et al. | 514/334 |
| 5,696,143 A | 12/1997 | Talley et al. | 514/403 |
| 5,710,140 A | 1/1998 | Ducharme et al. | 514/91 |
| 5,716,955 A | 2/1998 | Adams et al. | 514/235.8 |
| 5,723,485 A | 3/1998 | Güngör et al. | 514/415 |
| 5,739,166 A | 4/1998 | Reitz et al. | 514/602 |
| 5,741,798 A | 4/1998 | Lazer et al. | 514/309 |
| 5,756,499 A | 5/1998 | Adams et al. | 514/235.8 |
| 5,756,529 A | 5/1998 | Isakson et al. | 514/406 |
| 5,756,546 A | 5/1998 | Pirotte et al. | 514/605 |
| 5,776,967 A | 7/1998 | Kreft et al. | 514/411 |
| 5,783,597 A | 7/1998 | Beers et al. | 514/447 |
| 5,789,413 A | 8/1998 | Black et al. | 514/255 |
| 5,807,873 A | 9/1998 | Nicolaï et al. | 514/336 |
| 5,817,700 A | 10/1998 | Dube et al. | 514/768 |
| 5,830,911 A | 11/1998 | Failli et al. | 514/411 |
| 5,849,943 A | 12/1998 | Atkinson et al. | 560/8 |
| 5,859,036 A | 1/1999 | Sartori et al. | 514/369 |
| 5,861,419 A | 1/1999 | Dube et al. | 514/334 |
| 5,866,596 A | 2/1999 | Sartori et al. | 514/369 |
| 5,869,524 A | 2/1999 | Failli | 514/473 |
| 5,869,660 A | 2/1999 | Adams et al. | 544/122 |
| 5,883,267 A | 3/1999 | Rossen et al. | 549/319 |
| 5,892,053 A | 4/1999 | Zhi et al. | 548/377.1 |
| 5,922,742 A | 7/1999 | Black et al. | 514/345 |
| 5,929,076 A | 7/1999 | Adams et al. | 514/252 |
| 5,932,598 A * | 8/1999 | Talley et al. | 514/341 |
| 5,935,990 A | 8/1999 | Khanna et al. | 514/423 |
| 5,945,539 A | 8/1999 | Haruta et al. | 548/235 |
| 5,958,978 A | 9/1999 | Yamazaki et al. | 514/567 |
| 5,968,958 A | 10/1999 | Guay et al. | 514/337 |
| 5,972,950 A | 10/1999 | Nicolai et al. | 514/277 |
| 5,973,191 A | 10/1999 | Marnett et al. | 560/142 |
| 5,981,576 A | 11/1999 | Belley et al. | 514/473 |
| 5,994,381 A | 11/1999 | Haruta et al. | 514/374 |
| 6,002,014 A | 12/1999 | Haruta et al. | 548/235 |
| 6,004,960 A | 12/1999 | Li et al. | 514/247 |
| 6,005,000 A | 12/1999 | Hopper et al. | 514/473 |
| 6,020,343 A | 2/2000 | Belley et al. | 514/309 |
| 6,020,347 A | 2/2000 | DeLaszlo et al. | 514/331 |
| 6,034,256 A | 3/2000 | Carter et al. | 549/456 |
| 6,040,319 A | 3/2000 | Corley et al. | 514/334 |
| 6,040,450 A | 3/2000 | Davies et al. | 546/256 |
| 6,046,208 A | 4/2000 | Adams et al. | 514/274 |
| 6,046,217 A | 4/2000 | Friesen et al. | 514/347 |
| 6,054,455 A * | 4/2000 | Guess et al. | 514/231.2 |
| 6,057,319 A | 5/2000 | Black et al. | 514/242 |
| 6,063,804 A | 5/2000 | De Nanteuil et al. | 514/411 |
| 6,063,807 A | 5/2000 | Chabrier de Lassauniere et al. | 514/420 |
| 6,071,954 A | 6/2000 | LeBlanc et al. | 514/473 |
| 6,077,868 A | 6/2000 | Cook et al. | 514/560 |
| 6,077,869 A | 6/2000 | Sui et al. | 514/615 |
| 6,083,969 A | 7/2000 | Ferro et al. | 514/403 |
| 6,096,753 A | 8/2000 | Spohr et al. | 514/269 |
| 6,133,292 A | 10/2000 | Wang et al. | 514/336 |
| 6,403,830 B2 * | 6/2002 | Webber et al. | 562/557 |
| 6,551,584 B2 * | 4/2003 | Bandyopadhyay et al. | 424/78.04 |

FOREIGN PATENT DOCUMENTS

| | | |
|---|---|---|
| EP | 0 846 689 | 6/1998 |
| EP | 0 863 134 | 9/1998 |
| EP | 0 985 666 | 3/2000 |
| WO | WO 94/15932 | 7/1994 |
| WO | WO 96/19469 | 6/1996 |
| WO | WO 96/26921 | 9/1996 |
| WO | WO 96/31509 | 10/1996 |
| WO | WO 96/36623 | 11/1996 |
| WO | WO 96/38418 | 12/1996 |
| WO | WO 97/03953 | 2/1997 |
| WO | WO 97/10840 | 3/1997 |
| WO | WO 97/13755 | 4/1997 |
| WO | WO 97/13767 | 4/1997 |
| WO | WO 97/25048 | 7/1997 |
| WO | WO 97/30030 | 8/1997 |
| WO | WO 97/34882 | 9/1997 |
| WO | WO 97/46524 | 12/1997 |
| WO | WO 98/04527 | 2/1998 |
| WO | WO 98/06708 | 2/1998 |
| WO | WO 98/07425 | 2/1998 |
| WO | WO 98/17292 | 4/1998 |
| WO | WO 98/21195 | 5/1998 |
| WO | WO 98/22457 | 5/1998 |
| WO | WO 98/32732 | 7/1998 |
| WO | WO 98/41516 | 9/1998 |
| WO | WO 98/43966 | 10/1998 |
| WO | WO 98/45294 | 10/1998 |
| WO | WO 98/47871 | 10/1998 |
| WO | WO 99/01130 | 1/1999 |
| WO | WO 99/01131 | 1/1999 |
| WO | WO 99/01452 | 1/1999 |
| WO | WO 99/01455 | 1/1999 |
| WO | WO 99/10331 | 3/1999 |
| WO | WO 99/10332 | 3/1999 |
| WO | WO 99/11605 | 3/1999 |
| WO | WO 99/12930 | 3/1999 |
| WO | WO 99/14195 | 3/1999 |
| WO | WO 99/14205 | 3/1999 |
| WO | WO 99/15505 | 4/1999 |
| WO | WO 99/23087 | 5/1999 |
| WO | WO 99/24404 | 5/1999 |
| WO | WO 99/25695 | 5/1999 |
| WO | WO 9921585 | 6/1999 |
| WO | WO 9921598 | 6/1999 |
| WO | WO 99/35130 | 7/1999 |
| WO | WO 99/61016 | 12/1999 |
| WO | WO 99/61436 | 12/1999 |
| WO | WO 99/62884 | 12/1999 |
| WO | WO 99/64415 | 12/1999 |
| WO | WO 00/01380 | 1/2000 |
| WO | WO 00/08024 | 2/2000 |
| WO | WO 00/10993 | 3/2000 |
| WO | WO 00/13684 | 3/2000 |
| WO | WO 00/18741 | 4/2000 |
| WO | WO 00/18753 | 4/2000 |

| WO | WO 00/23426 | 4/2000 |
| WO | WO 00/24719 | 5/2000 |
| WO | WO 00/26216 | 5/2000 |
| WO | WO 00/31072 | 6/2000 |
| WO | WO 00/40087 | 7/2000 |
| WO | WO 00/56348 | 9/2000 |

OTHER PUBLICATIONS

Pharmaceutical Solutions III: Ophthalmic Solutions 1996, downloaded from the world wide web at pharmlabs.unc.edu/ophthalmics/text.htm on Jul. 14, 2006.*

Talley et al., 46 J. Med. Chem. 1661 (2000).*

Supporting information for Talley et al., 46 J. Med. Chem. 1661 (2000).*

Jain, K. K.., 9 Expert Opinions on Investigational Drugs 2717 (2000).*

(1995). *Remington: The Science and Practice of Pharmacy*, 19 ed., vol. 2. Mack Pub Co., pp. 1544-1546.

Jain (2000). Evaluation of intravenous parecoxib for the relief of acute post-surgical pain. In *Expert Opinion on Investigational Drugs*. 9(11), pp. 2717-2723.

Miller (1981). *Survival Analysis*, John Wiley & Sons, pp. 74-75.

Simon & Lee (1982). *Cancer Treat. Rep.* 66, pp. 37-42.

Aulton, M.,E., "Pharmaceutics: Science of Dosage Form Design", Churchhill Livingstone, 1998, pp. 368-369.

"Pharmacy", edited by Bi Dianzhou, People's Medical Publishing House, May 2000, the fourth edition, p. 268, 2, Process of Lyophilization., to line 12 from the bottom of p. 269.

Talley, J, et al., "N-[[(5-Methyl-3-phenylisoxazol-4-yl)-phenyl]sulfonyl]propanamide, Sodium Salt, Parecoxib Sodium: A Potent and Selective Inhibitor of COX-2 for Parenteral Administration", Journal of Medicinal Chemistry, 2000, pp. 1661-1663, No. 9, vol. 43.

* cited by examiner

RECONSTITUTABLE PARENTERAL COMPOSITION

This application claims priority of U.S. provisional application Ser. No. 60/281,058, filed on Apr. 3, 2001.

FIELD OF THE INVENTION

The present invention relates to water-soluble selective cyclooxygenase-2 (COX-2) inhibitory drugs and salts and prodrugs thereof and in particular to parecoxib, for example in the form of its sodium salt (parecoxib sodium). Parecoxib is a water-soluble prodrug of the selective COX-2 inhibitory drug valdecoxib. More particularly, the invention relates to parenterally deliverable, for example injectable, formulations of water-soluble selective COX-2 inhibitory drugs and salts and prodrugs thereof. Even more particularly, the invention relates to such formulations that are prepared as powders for reconstitution in an aqueous carrier prior to parenteral administration. The invention also relates to processes for preparing such reconstitutable formulations, to therapeutic methods of use of such formulations and to use of such formulations in manufacture of medicaments.

BACKGROUND OF THE INVENTION

Inhibition of cyclooxygenase (COX) enzymes is believed to be at least the primary mechanism by which nonsteroidal anti-inflammatory drugs (NSAIDs) exert their characteristic anti-inflammatory, antipyretic and analgesic effects, through inhibition of prostaglandin synthesis. Conventional NSAIDs such as ketorolac, diclofenac, naproxen and salts thereof inhibit both the constitutively expressed COX-1 and the inflammation-associated or inducible COX-2 isoforms of cyclooxygenase at therapeutic doses. Inhibition of COX-1, which produces prostaglandins that are necessary for normal cell function, appears to account for certain adverse side effects that have been associated with use of conventional NSAIDs. By contrast, selective inhibition of COX-2 without substantial inhibition of COX-1 leads to anti-inflammatory, antipyretic, analgesic and other useful therapeutic effects while minimizing or eliminating such adverse side effects. Selective COX-2 inhibitory drugs such as celecoxib and rofecoxib, first commercially available in 1999, have therefore represented a major advance in the art. These drugs are formulated in a variety of orally deliverable dosage forms.

Parenteral routes of administration, including subcutaneous, intramuscular and intravenous injection, offer numerous benefits over oral delivery in particular situations, for a wide variety of drugs. For example, parenteral administration of a drug typically results in attainment of a therapeutically effective blood serum concentration of the drug in a shorter time than is achievable by oral administration. This is especially true of intravenous injection, whereby the drug is placed directly in the bloodstream. Parenteral administration also results in more predictable blood serum concentrations of the drug, because losses in the gastrointestinal tract due to metabolism, binding to food and other causes are eliminated. For similar reasons, parenteral administration often permits dose reduction. Parenteral administration is generally the preferred method of drug delivery in emergency situations, and is also useful in treating subjects who are uncooperative, unconscious, or otherwise unable or unwilling to accept oral medication.

Relatively few NSAIDs are commercially available in injectable form. Non-selective NSAIDs such as ketorolac tromethamine salt that are available for parenteral use are effective analgesics but have been associated with side effects typical of such non-selective NSAIDs. These side effects have included upper gastrointestinal tract ulceration and bleeding, particularly in elderly subjects; reduced renal function, potentially leading to fluid retention and exacerbation of hypertension; and inhibition of platelet function, potentially predisposing the subject to increased bleeding, for example during surgery. Such side effects have seriously limited the use of parenteral formulations of non-selective NSAIDs.

It would therefore represent a further significant advance in the art if a parenterally deliverable formulation of a selective COX-2 inhibitory drug could be provided.

It is known to prepare parenteral formulations by a process of lyophilization (freeze-drying) of an aqueous solution of the therapeutic agent. See for example *Remington: The Science and Practice of Pharmacy*, 19th edition (1995), Mack Publishing, pp. 1544-1546. According to *Remington*, excipients often are added to the therapeutic agent to increase the amount of solids, so that the resulting powder is more readily visible when the amount of the therapeutic agent is very small. "Some consider it ideal for the dried-product plug to occupy essentially the same volume as that of the original solution. To achieve this, the solids content of the original product must be between approximately 5 and 25%. Among the substances found most useful for this purpose, usually as a combination, are sodium or potassium phosphates, citric acid, tartaric acid, gelatin and carbohydrates such as dextrose, mannitol and dextran." *Remington*, loc. cit.

Parecoxib, disclosed in U.S. Pat. No. 5,932,598 to Talley et al., is one of a class of water-soluble prodrugs of selective COX-2 inhibitory drugs. Parecoxib rapidly converts to the substantially water-insoluble selective COX-2 inhibitory drug valdecoxib following administration to a subject. Parecoxib also converts to valdecoxib upon exposure to water, for example upon dissolution in water. The high water solubility of parecoxib, particularly of salts of parecoxib such as the sodium salt, by comparison with most selective COX-2 inhibitory drugs such as celecoxib and valdecoxib, has led to interest in developing parecoxib for parenteral use. Parecoxib, having the structural formula (I) below, itself shows weak in vitro inhibitory activity against both COX-1 and COX-2, while valdecoxib (II) has strong inhibitory activity against COX-2 but is a weak inhibitor of COX-1.

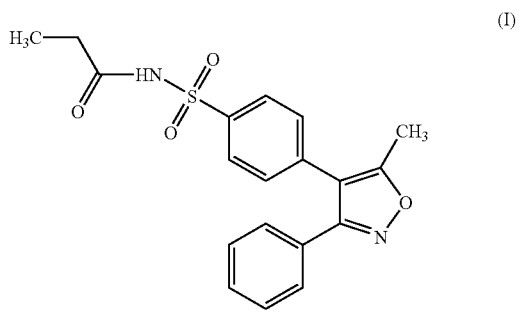

-continued

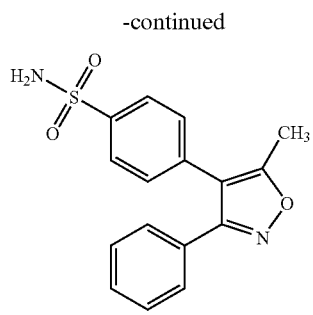

(II)

Other water-soluble selective COX-2 inhibitory drugs and prodrugs are known. For example, U.S. Pat. No. 6,034,256 to Carter et al. discloses a series of water-soluble benzopyrans said to be useful as selective COX-2 inhibitory drugs, including the compound (S)-6,8-dichloro-2-(trifluoromethyl)-2H-1-benzopyran-3-carboxylic acid (III) and salts thereof.

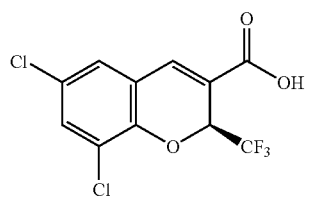

(III)

While these and other selective COX-2 inhibitory drugs and prodrugs have been proposed in general terms for parenteral administration, no pharmaceutically acceptable injectable formulation of such drugs or prodrugs has hitherto been described. As will be clear from the disclosure that follows, numerous problems have beset the formulator attempting to prepare such a formulation, illustratively of parecoxib. The present invention provides a solution to these problems.

SUMMARY OF THE INVENTION

There is now provided, in one embodiment, a pharmaceutical composition comprising, in powder form, (a) at least one water-soluble therapeutic agent selected from selective COX-2 inhibitory drugs and prodrugs and salts thereof, in a therapeutically effective total amount constituting about 30% to about 90% by weight, (b) a parenterally acceptable buffering agent in an amount of about 5% to about 60% by weight, and optionally (c) other parenterally acceptable excipient ingredients in a total amount not greater than about 10% by weight, of the composition. The composition is reconstitutable in a parenterally acceptable solvent liquid, preferably an aqueous liquid, to form an injectable solution.

The composition described above can be prepared by a process comprising a step of lyophilization of an aqueous solution comprising the therapeutic agent, the buffering agent and optionally other excipient ingredients to form a readily reconstitutable powder; such a process represents a further embodiment of the present invention.

A still further embodiment of the invention is an injectable solution prepared by reconstitution of the composition.

A still further embodiment of the invention is an article of manufacture comprising a sealed vial having contained therewithin a unit dosage amount of the composition in a sterile condition.

A still further embodiment of the invention is a method of treating or preventing a COX-2 mediated disease or disorder in a subject, the method comprising (a) reconstituting a unit dosage amount of the composition in a physiologically acceptable volume of a parenterally acceptable solvent liquid to form an injectable solution, and (b) injecting the solution parenterally into the subject.

In all of the above embodiments, an especially preferred therapeutic agent is a water-soluble salt of parecoxib. It is surprisingly found that parecoxib, upon parenteral administration, exhibits through conversion to valdecoxib substantially equal anti-inflammatory and analgesic effect at equal dose to valdecoxib itself. Thus, according to a yet further embodiment of the invention, there is provided a method of treating or preventing a COX-2 mediated disease or disorder in a subject, the method comprising parenterally administering parecoxib or a salt thereof to the subject at a parecoxib dosage equal in molar amount to a therapeutically effective dosage of valdecoxib.

A yet further embodiment of the invention is an article of manufacture comprising a sealed vial having contained therewithin a sterile parenterally deliverable composition that comprises parecoxib or a salt thereof in a parecoxib dosage amount equal to a therapeutically effective dosage of valdecoxib.

DETAILED DESCRIPTION OF THE INVENTION

Figure 1:
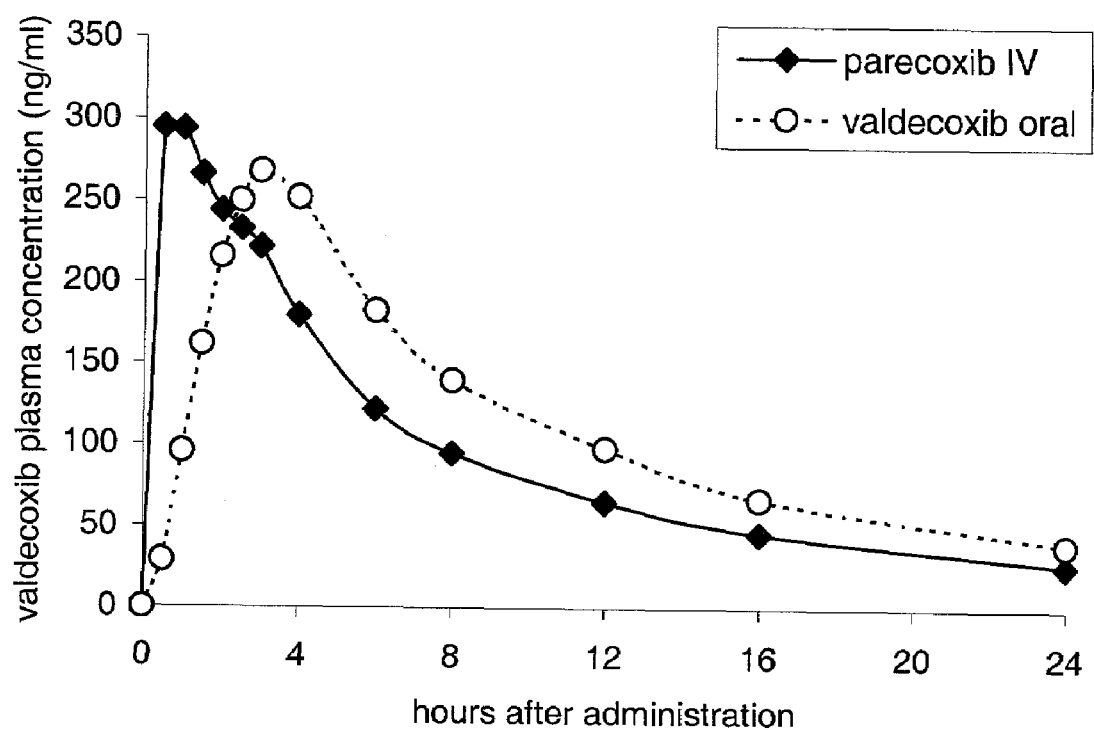
FIG. 1 presents data from the human pharmacokinetic study of Example 3, showing mean blood plasma concentrations of valdecoxib from 0 to 72 hours following (a) intravenous (IV) injection of 20 mg parecoxib in a 1 ml bolus; and (b) oral administration of 20 mg valdecoxib formulated as an immediate-release tablet.

A pharmaceutical composition of the present invention comprises as the therapeutic agent:
(a) a water-soluble selective COX-2 inhibitory drug;
(b) a water-soluble salt of a selective COX-2 inhibitory drug, whether or not such drug is itself water-soluble;
(c) a water-soluble prodrug of a selective COX-2 inhibitory drug, whether or not such drug is itself water-soluble; or
(d) a water-soluble salt of a prodrug of a selective COX-2 inhibitory drug, whether or not such prodrug is itself water-soluble.

More than one such therapeutic agent can be present, but in general it is preferred to include only one such selective COX-2 inhibitory drug or prodrug or salt thereof in the composition. A composition comprising a prodrug of a selective COX-2 inhibitory drug or a salt of such drug or prodrug may contain a small quantity of the drug itself, for example if the prodrug or salt readily converts to the drug during manufacture, storage, handling or use.

The term "water-soluble" as applied to a therapeutic agent herein means that the agent, in an amount that is therapeutically effective in a subject, is soluble in water at 20-25° C. and at a parenterally acceptable pH, the water being in a volume less than a maximum volume acceptable for parenteral administration of a single dose to the subject. Preferred therapeutic agents have a solubility in water at 20° C. and pH 7.4 of greater than about 0.1 mg/ml. More preferred therapeutic agents have a solubility in water at 20° C. and pH 7.4 of greater than about 0.5 mg/ml.

A selective COX-2 inhibitory drug useful herein, or to which a prodrug or salt useful herein is converted in vivo, exhibits selective inhibition of COX-2 relative to COX-1 with a selectivity factor of at least 50, preferably at least 100. Such drugs include without limitation compounds disclosed in the patents and publications listed below, each of which is individually incorporated herein by reference.

U.S. Pat. No. 5,344,991 to Reitz & Li.
U.S. Pat. No. 5,380,738 to Norman et al.
U.S. Pat. No. 5,393,790 to Reitz et al.
U.S. Pat. No. 5,401,765 to Lee.
U.S. Pat. No. 5,418,254 to Huang & Reitz.
U.S. Pat. No. 5,420,343 to Koszyk & Weier.
U.S. Pat. No. 5,434,178 to Talley & Rogier.
U.S. Pat. No. 5,436,265 to Black et al.
U.S. Pat. No. 5,466,823 to Talley et al.
U.S. Pat. No. 5,474,995 to Ducharme et al.
U.S. Pat. No. 5,475,018 to Lee & Bertenshaw.
U.S. Pat. No. 5,486,534 to Lee et al.
U.S. Pat. No. 5,510,368 to Lau et al.
U.S. Pat. No. 5,521,213 to Prasit et al.
U.S. Pat. No. 5,536,752 to Ducharme et al.
U.S. Pat. No. 5,543,297 to Cromlish et al.
U.S. Pat. No. 5,547,975 to Talley et al.
U.S. Pat. No. 5,550,142 to Ducharme et al.
U.S. Pat. No. 5,552,422 to Gauthier et al.
U.S. Pat. No. 5,585,504 to Desmond et al.
U.S. Pat. No. 5,593,992 to Adams et al.
U.S. Pat. No. 5,596,008 to Lee.
U.S. Pat. No. 5,604,253 to Lau et al.
U.S. Pat. No. 5,604,260 to Guay & Li.
U.S. Pat. No. 5,616,458 to Lipsky et al.
U.S. Pat. No. 5,616,601 to Khanna et al.
U.S. Pat. No. 5,620,999 to Weier et al.
U.S. Pat. No. 5,633,272 to Talley et al.
U.S. Pat. No. 5,639,780 to Lau et al.
U.S. Pat. No. 5,643,933 to Talley et al.
U.S. Pat. No. 5,658,903 to Adams et al.
U.S. Pat. No. 5,668,161 to Talley et al.
U.S. Pat. No. 5,670,510 to Huang & Reitz.
U.S. Pat. No. 5,677,318 to Lau.
U.S. Pat. No. 5,681,842 to Dellaria & Gane.
U.S. Pat. No. 5,686,460 to Nicolaï et al.
U.S. Pat. No. 5,686,470 to Weier et al.
U.S. Pat. No. 5,696,143 to Talley et al.
U.S. Pat. No. 5,710,140 to Ducharme et al.
U.S. Pat. No. 5,716,955 to Adams et al.
U.S. Pat. No. 5,723,485 to Guñgör & Teulon.
U.S. Pat. No. 5,739,166 to Reitz et al.
U.S. Pat. No. 5,741,798 to Lazer et al.
U.S. Pat. No. 5,756,499 to Adams et al.
U.S. Pat. No. 5,756,529 to Isakson & Talley.
U.S. Pat. No. 5,776,967 to Kreft et al.
U.S. Pat. No. 5,783,597 to Beers & Wachter.
U.S. Pat. No. 5,789,413 to Black et al.
U.S. Pat. No. 5,807,873 to Nicolaï & Teulon.
U.S. Pat. No. 5,817,700 to Dube et al.
U.S. Pat. No. 5,830,911 to Failli et al.
U.S. Pat. No. 5,849,943 to Atkinson & Wang.
U.S. Pat. No. 5,859,036 to Sartori et al.
U.S. Pat. No. 5,861,419 to Dube et al.
U.S. Pat. No. 5,866,596 to Sartori & Teulon.
U.S. Pat. No. 5,869,524 to Failli.
U.S. Pat. No. 5,869,660 to Adams et al.
U.S. Pat. No. 5,883,267 to Rossen et al.
U.S. Pat. No. 5,892,053 to Zhi et al.
U.S. Pat. No. 5,922,742 to Black et al.
U.S. Pat. No. 5,929,076 to Adams & Garigipati.
Above-cited U.S. Pat. No. 5,932,598.
U.S. Pat. No. 5,935,990 to Khanna et al.
U.S. Pat. No. 5,945,539 to Haruta et al.
U.S. Pat. No. 5,958,978 to Yamazaki et al.
U.S. Pat. No. 5,968,958 to Guay et al.
U.S. Pat. No. 5,972,950 to Nicolaï & Teulon.
U.S. Pat. No. 5,973,191 to Marnett & Kalgutkar.
U.S. Pat. No. 5,981,576 to Belley et al.
U.S. Pat. No. 5,994,381 to Haruta et al.
U.S. Pat. No. 6,002,014 to Haruta et al.
U.S. Pat. No. 6,004,960 to Li et al.
U.S. Pat. No. 6,005,000 to Hopper et al.
U.S. Pat. No. 6,020,343 to Belley et al.
U.S. Pat. No. 6,020,347 to DeLaszlo & Hagmann.
Above-cited U.S. Pat. No. 6,034,256.
U.S. Pat. No. 6,040,319 to Corley et al.
U.S. Pat. No. 6,040,450 to Davies et al.
U.S. Pat. No. 6,046,208 to Adams et al.
U.S. Pat. No. 6,046,217 to Friesen et al.
U.S. Pat. No. 6,057,319 to Black et al.
U.S. Pat. No. 6,063,804 to De Nanteuil et al.
U.S. Pat. No. 6,063,807 to Chabrier de Lassauniere & Broquet.
U.S. Pat. No. 6,071,954 to LeBlanc et al.
U.S. Pat. No. 6,077,868 to Cook et al.
U.S. Pat. No. 6,077,869 to Sui & Wachter.
U.S. Pat. No. 6,083,969 to Ferro et al.
U.S. Pat. No. 6,096,753 to Spohr et al.
U.S. Pat. No. 6,133,292 to Wang et al.
International Patent Publication No. WO 94/15932.
International Patent Publication No. WO 96/19469.
International Patent Publication No. WO 96/26921.
International Patent Publication No. WO 96/31509.
International Patent Publication No. WO 96/36623.
International Patent Publication No. WO 96/38418.
International Patent Publication No. WO 97/03953.
International Patent Publication No. WO 97/10840.
International Patent Publication No. WO 97/13755.
International Patent Publication No. WO 97/13767.
International Patent Publication No. WO 97/25048.
International Patent Publication No. WO 97/30030.
International Patent Publication No. WO 97/34882.
International Patent Publication No. WO 97/46524.
International Patent Publication No. WO 98/04527.
International Patent Publication No. WO 98/06708.
International Patent Publication No. WO 98/07425.
International Patent Publication No. WO 98/17292.
International Patent Publication No. WO 98/21195.
International Patent Publication No. WO 98/22457.
International Patent Publication No. WO 98/32732.
International Patent Publication No. WO 98/41516.
International Patent Publication No. WO 98/43966.
International Patent Publication No. WO 98/45294.
International Patent Publication No. WO 98/47871.
International Patent Publication No. WO 99/01130.
International Patent Publication No. WO 99/01131.
International Patent Publication No. WO 99/01452.
International Patent Publication No. WO 99/01455.
International Patent Publication No. WO 99/10331.
International Patent Publication No. WO 99/10332.
International Patent Publication No. WO 99/11605.
International Patent Publication No. WO 99/12930.
International Patent Publication No. WO 99/14195.
International Patent Publication No. WO 99/14205.
International Patent Publication No. WO 99/15505.
International Patent Publication No. WO 99/23087.
International Patent Publication No. WO 99/24404.
International Patent Publication No. WO 99/25695.

International Patent Publication No. WO 99/35130.
International Patent Publication No. WO 99/61016.
International Patent Publication No. WO 99/61436.
International Patent Publication No. WO 99/62884.
International Patent Publication No. WO 99/64415.
International Patent Publication No. WO 00/01380.
International Patent Publication No. WO 00/08024.
International Patent Publication No. WO 00/10993.
International Patent Publication No. WO 00/13684.
International Patent Publication No. WO 00/18741.
International Patent Publication No. WO 00/18753.
International Patent Publication No. WO 00/23426.
International Patent Publication No. WO 00/24719.
International Patent Publication No. WO 00/26216.
International Patent Publication No. WO 00/31072.
International Patent Publication No. WO 00/40087.
International Patent Publication No. WO 00/56348.
European Patent Application No. 0 799 823.
European Patent Application No. 0 846 689.
European Patent Application No. 0 863 134.
European Patent Application No. 0 985 666.

A preferred selective COX-2 inhibitory drug useful herein, or to which a prodrug or salt useful herein is converted in vivo, is a compound of formula (IV):

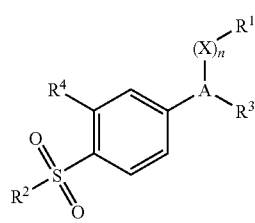

(IV)

wherein:

A is a substituent selected from partially unsaturated or unsaturated heterocyclyl and partially unsaturated or unsaturated carbocyclic rings, preferably a heterocyclyl group selected from pyrazolyl, furanonyl, isoxazolyl, pyridinyl, cyclopentenonyl and pyridazinonyl groups;

X is O, S or $CH_2$;

n is 0 or 1;

$R^1$ is at least one substituent selected from heterocyclyl, cycloalkyl, cycloalkenyl and aryl, and is optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;

$R^2$ is methyl, amino or aminocarbonylalkyl;

$R^3$ is one or more radicals selected from hydrido, halo, alkyl, alkenyl, alkynyl, oxo, cyano, carboxyl, cyanoalkyl, heterocyclyloxy, alkyloxy, alkylthio, alkylcarbonyl, cycloalkyl, aryl, haloalkyl, heterocyclyl, cycloalkenyl, aralkyl, heterocyclylalkyl, acyl, alkylthioalkyl, hydroxyalkyl, alkoxycarbonyl, arylcarbonyl, aralkylcarbonyl, aralkenyl, alkoxyalkyl, arylthioalkyl, aryloxyalkyl, aralkylthioalkyl, aralkoxyalkyl, alkoxyaralkoxyalkyl, alkoxycarbonylalkyl, aminocarbonyl, aminocarbonylalkyl, alkylaminocarbonyl, N-arylaminocarbonyl, N-alkyl-N-arylaminocarbonyl, alkylaminocarbonylalkyl, carboxyalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl and N-alkyl-N-arylaminosulfonyl, $R^3$ being optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio; and $R^4$ is selected from hydrido and halo.

Compositions of the invention are especially useful for water-soluble salts, prodrugs and salts of prodrugs of selective COX-2 inhibitory drugs having the formula (V):

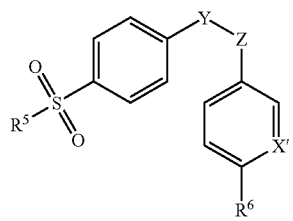

(V)

where $R^5$ is a methyl or amino group, $R^6$ is hydrogen or a $C_{1-4}$ alkyl or alkoxy group, X' is N or $CR^7$ where $R^7$ is hydrogen or halogen, and Y and Z are independently carbon or nitrogen atoms defining adjacent atoms of a five- to six-membered ring that is optionally substituted at one or more positions with oxo, halo, methyl or halomethyl groups, or an isomer or tautomer thereof. Preferred such five- to six-membered rings are cyclopentenone, furanone, methylpyrazole, isoxazole and pyridine rings substituted at no more than one position.

Illustratively, compositions of the invention are suitable for water-soluble salts, prodrugs and salts of prodrugs of celecoxib, deracoxib, valdecoxib, rofecoxib, etoricoxib, 2-(3,5-difluorophenyl)-3-[4-(methylsulfonyl)phenyl]-2-cyclopenten-1-one and 2-(3,4-difluorophenyl)-4-(3-hydroxy-3-methyl-1-butoxy)-5-[4-(methylsulfonyl)phenyl]-3-(2H)-pyridazinone, most particularly valdecoxib. A particularly useful prodrug of valdecoxib for use in compositions of the invention is parecoxib, more particularly a water-soluble salt thereof, for example parecoxib sodium.

Parecoxib used in compositions and methods of the invention can illustratively be prepared in the manner set forth in above-cited U.S. Pat. No. 5,932,598.

Compositions of the invention are also useful for compounds having the formula (VI):

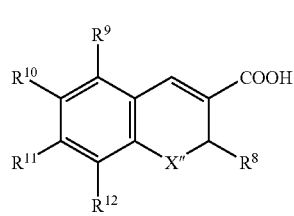

(VI)

where X" is O, S or N-lower alkyl; $R^8$ is lower haloalkyl; $R^9$ is hydrogen or halogen; $R^{10}$ is hydrogen, halogen, lower alkyl, lower alkoxy or haloalkoxy, lower aralkylcarbonyl, lower dialkylaminosulfonyl, lower alkylaminosulfonyl, lower aralkylaminosulfonyl, lower heteroaralkylaminosulfonyl, or 5- or 6-membered nitrogen-containing heterocyclosulfonyl; and $R^{11}$ and $R^{12}$ are independently hydrogen, halogen, lower alkyl, lower alkoxy, or aryl; and for pharmaceutically acceptable salts thereof.

A particularly useful compound of formula (VI) is (S)-6,8-dichloro-2-(trifluoromethyl)-2H-1-benzopyran-3-carboxylic acid, particularly in the form of a water-soluble salt thereof, for example the sodium salt. This compound can illustratively be prepared in the manner set forth in above-cited U.S. Pat. No. 6,034,256.

One or more therapeutic agents selected from those disclosed hereinabove are present in a reconstitutable powder composition of the invention in a total amount of about 30% to about 90%, preferably about 40% to about 85%, and more preferably about 50% to about 80%, by weight of the composition.

The buffering agent, which is present in an amount of about 5% to about 60%, preferably about 10% to about 60%, and more preferably about 20% to about 50%, by weight of the composition, is typically the predominant excipient ingredient. In one embodiment of the invention, the reconstitutable powder composition consists essentially of the therapeutic agent and the buffering agent.

The buffering agent is selected to provide a pH of the composition, upon reconstitution in a physiologically acceptable volume of a parenterally acceptable solvent liquid, that (a) is parenterally acceptable, (b) is consistent with the therapeutic agent being entirely in solution in the solvent liquid, and (c) provides a medium wherein the therapeutic agent exhibits acceptable chemical stability for at least about one hour following reconstitution. Suitable buffering agents can illustratively be selected from sodium and potassium phosphates, sodium and potassium citrates, mono-, di- and triethanolamines, 2-amino-2-(hydroxymethyl)-1,3-propanediol (tromethamine), etc. and mixtures thereof. Preferred buffering agents are dibasic sodium and potassium phosphates and tromethamine. An especially preferred buffering agent is dibasic sodium phosphate, for example dibasic sodium phosphate anhydrous, heptahydrate, dodecahydrate, etc.

In one embodiment, the pH of the composition upon reconstitution is about 7 to about 9, preferably about 7.5 to about 8.5, for example about 8. If desired, pH can be adjusted by including in the composition, in addition to the buffering agent, a small amount of an acid, for example phosphoric acid, and/or a base, for example sodium hydroxide.

Excipients other than the buffering agent, if present, constitute not more than about 10%, preferably not more than about 5%, by weight of the composition prior to reconstitution. The term "excipient" herein embraces all non-therapeutically active components of the composition except for water. In one embodiment of the invention, no excipients other than the buffering agent are substantially present.

Surprisingly, it has been found important to include in the composition no more than about 10% by weight, preferably no more than about 5% by weight, and most preferably substantially no amount, of ingredients commonly used as bulking agents in reconstitutable parenteral formulations, other than buffering agents. In particular, the widely used bulking agent mannitol is preferably excluded from the composition, or if included, is present at no more than about 10%, preferably no more than about 5%, by weight of the composition. According to the present invention, it is believed that by minimizing the amount of, or excluding altogether, such bulking agents, especially mannitol, as components of the composition, acceptable chemical stability of the therapeutic agent can be assured.

Optionally, one or more preservatives can be included in the composition at up to about 0.5% by weight. Suitable illustrative preservatives include methylparaben, propylparaben, phenol and benzyl alcohol.

A reconstitutable powder composition of the invention preferably contains less than about 5%, more preferably less than about 2%, and most preferably less than about 1%, by weight of water. Typically the moisture content is about 0.5% to about 1% by weight. It is especially important to keep the amount of water to such a low level where the therapeutic agent has a tendency to degrade or convert to a less soluble form in presence of water. Powder compositions of the invention exhibit acceptable chemical stability of the therapeutic agent for at least about 30 days, preferably at least about 6 months, most preferably at least about 2 years, when stored at room temperature (about 20-25° C.) in a sealed vial.

"Acceptable chemical stability" herein means that the composition, following the defined time period (e.g., about 30 days, about 6 months or about 2 years), passes a standard test for chemical purity of the therapeutic agent, for example as may be required for approval by a regulatory authority. An example of such a test is the "5% total, 1% single impurity rule", whereby a preparation of a candidate drug must contain not more than 5% total impurities, and not more than 1% of any single impurity.

Where the therapeutic agent is parecoxib, for example in the form of parecoxib sodium, partial conversion to valdecoxib can occur in a composition over a period of time. As valdecoxib is itself therapeutically active as a selective COX-2 inhibitory drug (indeed the therapeutic efficacy of parecoxib is dependent upon conversion in the body to valdecoxib), such conversion does not result in a loss of therapeutic effect. However, as valdecoxib has extremely low solubility in water, it is desirable to minimize such conversion prior to reconstitution, so that complete dissolution of the therapeutic agent is assured. The presence of particulates, such as would result from the presence of significant quantities of valdecoxib, is generally undesirable in a solution intended for parenteral administration.

It is surprisingly found that conversion of parecoxib to valdecoxib in a reconstitutable powder composition can be greatly reduced by reduction or, preferably, elimination from the composition of bulking agents such as mannitol. This is illustrated in Examples 1 and 2 hereinbelow. Compositions of the invention, having no more than 10% by weight of excipients other than buffering agents, exhibit a very high degree of chemical stability of parecoxib, as shown in Example 1, whereas compositions having higher levels of excipients other than buffering agents exhibit a greater degree of conversion of parecoxib to valdecoxib, as shown in Example 2.

An injectable solution composition prepared by reconstituting a powder composition as herein provided in a parenterally acceptable solvent, preferably an aqueous solvent, is a further embodiment of the present invention. In such a solution composition the therapeutic agent can have limited chemical stability, in which case it is preferred to reconstitute the composition within a short period of time, for example within about one hour, before administration. In other cases the therapeutic agent can exhibit a relatively high degree of chemical stability in solution, and in such cases it is not critical to administer within a short period of time after reconstitution.

Where the therapeutic agent is parecoxib, for example in the form of parecoxib sodium, partial conversion to highly insoluble valdecoxib can occur in aqueous solution over a period of time, resulting in formation of solid particulates. As indicated above, the presence of solid particulates is generally undesirable in injectable formulations; thus in the particular case of parecoxib compositions of the invention, injectable solutions are preferably administered within a short period of time, for example within about one hour, following reconstitution.

Rate of conversion of parecoxib to valdecoxib in an aqueous medium can be greatly reduced by maintaining the medium at a pH of about 7 or higher. Furthermore, aqueous solubility of parecoxib sodium itself is strongly affected by pH. For example, equilibrium solubility at 20° C. rises from 1.0 mg/ml at pH 7.3 to 18 mg/ml at pH 7.8 and to 220 mg/ml at pH 8.2. Supersaturated solutions of parecoxib sodium can also be prepared at much higher concentrations. A preferred pH range providing physiological acceptability, good short-term chemical stability and good solubility of parecoxib sodium is about 7.5 to about 8.5, more preferably about 7.8 to about 8.2, for example about 8.0.

Any known parenterally acceptable solvent liquid can be used to reconstitute a powder composition of the invention. Water for injection can be suitable, but will generally provide a hypotonic solution. Accordingly, it is generally preferred to use an aqueous liquid containing a solute such as dextrose or sodium chloride. Illustratively, 0.9% sodium chloride injection USP, bacteriostatic 0.9% sodium chloride injection USP, 5% dextrose injection USP, and 5% dextrose and 0.45% sodium chloride injection USP are suitable. Lactated Ringer's injection USP is less suitable, at least where the therapeutic agent is parecoxib sodium, because of a tendency to form crystals.

A suitable volume of the solvent liquid for reconstitution depends on the age and body weight of the subject, the solubility and dosage amount of the therapeutic agent and other factors, but is generally about 0.25 ml to about 5 ml, preferably about 0.5 ml to about 2 ml. For example, in the case of parecoxib sodium, a 20 mg dose can generally be conveniently reconstituted in about 1 ml of any of the above solvent liquids, while for a 40 mg dose a 2 ml volume of the solvent liquid is generally suitable.

A powder composition of the invention preferably has sufficient porosity to permit rapid dissolution of the therapeutic agent upon reconstitution in the solvent liquid. A high degree of porosity is obtainable by using a process to prepare the powder as described hereinbelow. Such a process is a further embodiment of the present invention and is described herein with particular reference to parecoxib sodium and dibasic sodium phosphate heptahydrate; however, it will be understood that the process can be readily adapted to other therapeutic agents and/or other buffering agents in accordance with the invention.

In this process, parecoxib sodium and dibasic sodium phosphate heptahydrate as buffering agent are dissolved in water to form an aqueous solution. Preferably water for injection is used as the solvent. Parecoxib sodium and the buffering agent are present in the solution at concentrations relative to each other consistent with the desired relative concentrations of these ingredients in the final composition. Absolute concentrations of these ingredients are not critical; however, in the interest of process efficiency it is generally preferred that the concentration of parecoxib sodium be as high as can be conveniently prepared without risking exceeding the limit of solubility. Other formulation ingredients can be added in this step if desired. Order of addition is not critical but it is strongly preferred to add the parecoxib sodium last to ensure rapid and complete dissolution.

The solution is optionally but preferably sterilized, for example by passing through one or more sterilizing filters, and is then metered into one or more vials. Each vial receives a measured volume of solution having a desired unit dosage amount of parecoxib sodium. Lyophilization stoppers having an opening to allow sublimation to occur are placed on the vials. Preferably the vials and stoppers are sterile and filling is conducted under aseptic conditions.

The stoppered vials are then placed in a lyophilization chamber and the contents of the vials lyophilized, preferably in a three-phase cycle.

In a first phase of the lyophilization cycle, the solution in each vial is frozen to a temperature below the glass transition temperature of the solution. For compositions of the invention comprising parecoxib sodium and dibasic sodium phosphate, the glass transition temperature is about −20° C. Glass transition temperature can be measured by any technique known in the art, for example by use of a freeze-drying microscope or by electrical resistance measurement. A suitable temperature for this freezing phase is typically about −30° C. to about −60° C., for example about −40° C. to about −50° C. Temperature is gradually lowered from room temperature to the desired freezing temperature, typically over a period of about 1 to about 5 hours, more typically about 2 to about 4 hours. The temperature is then held at the freezing temperature, typically for a period of about 0.5 to about 24 hours, more typically about 0.75 to about 3 hours.

In the freezing phase of a preferred lyophilization process, temperature is first lowered from room temperature to about −20° C. fairly rapidly, e.g., over a period of about 0.25 to about 1 hour, more preferably about 0.5 to about 0.75 hour. Temperature is then lowered more gradually from about −20° C. to about −30° C., e.g., over a period of about 1 to about 4 hours, more preferably about 1.5 to about 3 hours. Without being bound by theory, it is believed that this gradual lowering of temperature ensures that the solution is completely frozen. Temperature is then lowered fairly rapidly from about −30° C. to the final freezing temperature, preferably about −40° C., e.g., over a period of about 0.1 to about 1 hour, more preferably about 0.25 to about 0.5 hour. It has been found that a stepwise freezing phase as described above tends to provide a final lyophilized product that appears solid with no cracking.

In a second phase of the lyophilization cycle, freeze-drying is effected by drawing a vacuum in the lyophilization chamber. This phase is described herein as the "primary drying" phase. A vacuum of about 25 to about 500 μm Hg (about 25 to about 500 millitorr), preferably about 50 to about 300 μm Hg, is generally suitable. During the primary drying phase, temperature is gradually raised, optionally in stages separated by periods when the temperature is held constant. Preferably the vacuum is maintained with a nitrogen sweep. Ice sublimates from the frozen solution during this phase, forming a partially dried cake.

In the primary drying phase of a preferred lyophilization process, temperature is first raised from the freezing temperature, e.g., about −40° C., to about 0° C. over a period of about 1 to about 5 hours, preferably about 2 to about 4 hours, and is then held at about 0° C. for a prolonged period, for example about 6 to about 12 hours, preferably about 8 to about 10 hours. Preferably a vacuum of about 150 to about 300 μm Hg is used during the primary drying phase.

In a third phase of the lyophilization cycle, drying is completed under vacuum. This phase is described herein as the "secondary drying" phase. Again a vacuum of about 25 to about 500 μm Hg, preferably about 50 to about 300 μm Hg, is generally suitable, preferably maintained with a nitrogen sweep. Temperature is raised during the secondary drying phase, preferably to a level above room temperature, for example about 40° C., to drive off remaining moisture and provide a powder having a moisture content of less than about 5%, preferably less than about 2%, more preferably less than about 1%, by weight.

In the secondary drying phase of a preferred lyophilization process, temperature is first raised from about 0° C. to about 40° C. over a period of about 1 to about 4 hours, preferably about 1.5 to about 3 hours, and is then held at about 40° C. for about 3 to about 12 hours, preferably about 4 to about 8 hours. Preferably a vacuum of about 150 to about 300 µm Hg is used during the secondary drying phase. Optionally during the last part of the secondary drying phase, while temperature is being held at about 40° C., the vacuum is lowered to about 25 to about 75 µm Hg.

The overall lyophilization cycle time is typically about 18 to about 36 hours. Extending the cycle time is generally not deleterious to quality of the finished product but increases process cost. The best combination of product quality and process economics can be found by routine testing based on the information presented herein, and will vary depending on several factors, including the particular lyophilization equipment used, the precise composition and concentration of ingredients in the solution being lyophilized, the therapeutic agent and buffering agent selected, etc. In general, however, a cycle time of about 18 to about 24 hours will be found suitable. In the case of parecoxib sodium compositions having dibasic sodium phosphate as the buffering agent, it has been found that shortening cycle time substantially below about 18 hours, for example to 16.5 hours, leads to increased incidence of collapse of the finished product, which in turn is not conducive to the desired rapid dissolution upon reconstitution.

On completion of the lyophilization cycle, the vacuum is released and temperature is permitted to return to room temperature. The vials are then capped and sealed to prevent reabsorption of moisture from the atmosphere and to maintain sterility.

An article of manufacture comprising a sealed vial, preferably a glass vial, having enclosed therewithin a powder composition as herein provided in a unit dosage amount and in a sterile condition, is a further embodiment of the present invention. In a particular embodiment, such an article of manufacture is provided, prepared by a process as described above. The vial preferably has a capacity sufficient to enable reconstitution of the composition in situ. Generally a capacity of about 1 ml to about 10 ml, preferably about 2 ml to about 5 ml, will be found convenient.

The term "vial" herein is used to denote any small container, having a closure, that is suitable for packaging a unit dosage amount of a reconstitutable powder, preferably in a sterile condition. It will be understood that equivalent forms of packaging, such as an ampoule, a disposable syringe and a syringe cartridge, are encompassed by this embodiment of the invention.

Optionally the vial can comprise two compartments, one to contain the reconstitutable powder and one to contain a solvent liquid in an amount sufficient to dissolve the powder. In such a vial the two compartments are interconnected by an aperture wherein a stopper can be engaged to prevent contact of the powder and the solvent liquid until the vial is ready for use. In use, the liquid is brought into contact with the powder by disengagement or puncture of the stopper by any suitable means, for example a device such as a plunger that exerts pressure or drives a needle through the stopper. Examples of such multi-compartment vials include a dual-chamber cartridge for a syringe and a dual-chamber vial such as that available under the trademark Act-O-Vial® of Pharmacia Corporation.

A unit dosage amount of a powder composition of the invention, suitable for preparation and or placement in a vial to form an article of manufacture of the invention, is an amount that comprises sufficient of the therapeutic agent to provide a therapeutic benefit upon parenteral administration to a subject having a COX-2 mediated condition or disorder. For example, in the case of a parecoxib sodium composition of the invention, a suitable unit dosage amount is generally one containing about 1 mg to about 200 mg, preferably about 5 mg to about 120 mg, and more preferably about 10 mg to about 100 mg, for example about 20 mg, about 40 mg or about 80 mg, parecoxib. Where the therapeutic agent is other than parecoxib, a suitable unit dosage amount is one that is therapeutically equivalent to parecoxib at the dosage ranges indicated above.

Compositions of the invention are useful in treatment and prevention of a very wide range of disorders mediated by COX-2, including but not restricted to disorders characterized by inflammation, pain and/or fever. Such compositions are especially useful as anti-inflammatory agents, such as in treatment of arthritis, with the additional benefit of having significantly less harmful side effects than compositions of conventional NSAIDs that lack selectivity for COX-2 over COX-1. In particular, compositions of the invention have reduced potential for gastrointestinal toxicity and gastrointestinal irritation, including upper gastrointestinal ulceration and bleeding, by comparison with compositions of conventional NSAIDs. Thus compositions of the invention are particularly useful as an alternative to conventional NSAIDs where such NSAIDs are contraindicated, for example in patients with peptic ulcers, gastritis, regional enteritis, ulcerative colitis, diverticulitis or with a recurrent history of gastrointestinal lesions; gastrointestinal bleeding, coagulation disorders including anemia such as hypoprothrombinemia, hemophilia or other bleeding problems; kidney disease; or in patients prior to surgery or patients taking anticoagulants.

Contemplated compositions are useful to treat a variety of arthritic disorders, including but not limited to rheumatoid arthritis, spondyloarthropathies, gouty arthritis, osteoarthritis, systemic lupus erythematosus and juvenile arthritis.

Such compositions are useful in treatment of asthma, bronchitis, menstrual cramps, preterm labor, tendinitis, bursitis, allergic neuritis, cytomegalovirus infection, apoptosis including HIV-induced apoptosis, lumbago, liver disease including hepatitis, skin-related conditions such as psoriasis, eczema, acne, burns, dermatitis and ultraviolet radiation damage including sunburn, and post-operative inflammation including that following ophthalmic surgery such as cataract surgery or refractive surgery.

Such compositions are useful to treat gastrointestinal conditions such as inflammatory bowel disease, Crohn's disease, gastritis, irritable bowel syndrome and ulcerative colitis.

Such compositions are useful in treating inflammation in such diseases as migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, and the like.

Such compositions are useful in treatment of ophthalmic disorders, including without limitation inflammatory disorders such as endophthalmitis, episcleritis, retinitis, iriditis, cyclitis, choroiditis, keratitis, conjunctivitis and blepharitis, inflammatory disorders of more than one part of the eye, e.g., retinochoroiditis, iridocyclitis, iridocyclochoroiditis (also known as uveitis), keratoconjunctivitis, blepharoconjunctivitis, etc.; other COX-2 mediated retinopathies including diabetic retinopathy; ocular photophobia; acute trauma of any tissue of the eye including postsurgical trauma, e.g., following cataract or corneal transplant surgery; postsurgical ocular inflammation; intraoperative miosis; corneal graft rejection; ocular, for example retinal, neovascularization including that following injury or infection; macular degeneration; cystoid macular edema; retrolental fibroplasia; neovascular glaucoma; and ocular pain.

Such compositions are useful in treatment of pulmonary inflammation, such as that associated with viral infections and cystic fibrosis, and in bone resorption such as that associated with osteoporosis.

Such compositions are useful for treatment of certain central nervous system disorders, such as cortical dementias including Alzheimer's disease, neurodegeneration, and central nervous system damage resulting from stroke, ischemia and trauma. The term "treatment" in the present context includes partial or total inhibition of dementias, including Alzheimer's disease, vascular dementia, multi-infarct dementia, pre-senile dementia, alcoholic dementia and senile dementia.

Such compositions are useful in treatment of allergic rhinitis, respiratory distress syndrome, endotoxin shock syndrome and liver disease.

Such compositions are useful in treatment of pain, including but not limited to postoperative pain, dental pain, muscular pain, and pain resulting from cancer. For example, such compositions are useful for relief of pain, fever and inflammation in a variety of conditions including rheumatic fever, influenza and other viral infections including common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, and trauma following surgical and dental procedures.

Such compositions are useful for treating and preventing inflammation-related cardiovascular disorders, including vascular diseases, coronary artery disease, aneurysm, vascular rejection, arteriosclerosis, atherosclerosis including cardiac transplant atherosclerosis, myocardial infarction, embolism, stroke, thrombosis including venous thrombosis, angina including unstable angina, coronary plaque inflammation, bacterial-induced inflammation including Chlamydia-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries.

Such compositions are useful in treatment of angiogenesis-related disorders in a subject, for example to inhibit tumor angiogenesis. Such compositions are useful in treatment of neoplasia, including metastasis; ophthalmological conditions such as corneal graft rejection, ocular neovascularization, retinal neovascularization including neovascularization following injury or infection, diabetic retinopathy, macular degeneration, retrolental fibroplasia and neovascular glaucoma; ulcerative diseases such as gastric ulcer; pathological, but non-malignant, conditions such as hemangiomas, including infantile hemangiomas, angiofibroma of the nasopharynx and avascular necrosis of bone; and disorders of the female reproductive system such as endometriosis.

Such compositions are useful in prevention and treatment of benign and malignant tumors and neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer, stomach cancer, colon cancer, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers that effect epithelial cells throughout the body. Neoplasias for which compositions of the invention are contemplated to be particularly useful are gastrointestinal cancer, Barrett's esophagus, liver cancer, bladder cancer, pancreatic cancer, ovarian cancer, prostate cancer, cervical cancer, lung cancer, breast cancer and skin cancer. Such compositions can also be used to treat fibrosis that occurs with radiation therapy. Such compositions can be used to treat subjects having adenomatous polyps, including those with familial adenomatous polyposis (FAP). Additionally, such compositions can be used to prevent polyps from forming in subjects at risk of FAP.

Such compositions inhibit prostanoid-induced smooth muscle contraction by inhibiting synthesis of contractile prostanoids and hence can be of use in treatment of dysmenorrhea, premature labor, asthma and eosinophil-related disorders. They also can be of use for decreasing bone loss particularly in postmenopausal women (i.e., treatment of osteoporosis), and for treatment of glaucoma.

Preferred uses for compositions of the invention are for treatment of rheumatoid arthritis and osteoarthritis, for pain management generally (particularly post-oral surgery pain, post-general surgery pain, post-orthopedic surgery pain, and acute flares of osteoarthritis), for treatment of Alzheimer's disease, and for colon cancer chemoprevention.

Besides being useful for human treatment, compositions of the invention are useful for veterinary treatment of companion animals, exotic animals, farm animals, and the like, particularly mammals. More particularly, compositions of the invention are useful for treatment of COX-2 mediated disorders in horses, dogs and cats.

The present invention is further directed to a therapeutic method of treating a condition or disorder where treatment with a COX-2 inhibitory drug is indicated, the method comprising parenteral administration of a reconstituted composition of the invention to a subject in need thereof. The dosage regimen to prevent, give relief from, or ameliorate the condition or disorder preferably corresponds to once-a-day or twice-a-day treatment, but can be modified in accordance with a variety of factors. These include the type, age, weight, sex, diet and medical condition of the subject and the nature and severity of the disorder. Thus, the dosage regimen actually employed can vary widely and can therefore deviate from the preferred dosage regimens set forth above.

Initial treatment can begin with a dose regimen as indicated above. Treatment is generally continued as necessary over a period of several weeks to several months or years until the condition or disorder has been controlled or eliminated. Subjects undergoing treatment with a reconstituted composition of the invention can be routinely monitored by any of the methods well known in the art to determine effectiveness of therapy. Continuous analysis of data from such monitoring permits modification of the treatment regimen during therapy so that optimally effective doses are administered at any point in time, and so that the duration of treatment can be determined. In this way, the treatment regimen and dosing schedule can be rationally modified over the course of therapy so that the lowest amount of the composition exhibiting satisfactory effectiveness is administered, and so that administration is continued only for so long as is necessary to successfully treat the condition or disorder.

The term "parenteral administration" herein encompasses injection and/or infusion of a composition into or through the skin of a subject, and includes intradermal, subcutaneous, intramuscular, intravenous, intramedullary, intra-articular, intrasynovial, intraspinal, intrathecal and intracardiac administration. Any known device useful for parenteral injection or infusion of drugs can be used to effect such administration.

It has been found that parecoxib, when administered parenterally to a human subject, is rapidly and completely converted to valdecoxib. Surprisingly, therefore, even where rapid onset of therapeutic effect is desired, a therapeutically effective dose of parecoxib, for example in the form of parecoxib sodium, is one that is equal to a therapeutically effective dose of valdecoxib administered orally. The term "equal" in this context means equal in molar amount or in absolute amount (i.e., in weight). Based on molecular weights, complete conversion of 1 mg parecoxib produces about 0.85 mg valdecoxib. For practical purposes, no great error arises from considering 1 mg parecoxib to be equivalent to 1 mg valdecoxib.

Thus according to an embodiment of the present invention, a method is provided for treatment of a COX-2 mediated disorder in a human subject comprising parenterally administering parecoxib or a salt thereof to the subject at a parecoxib dosage equal to a therapeutically effective dosage of valdecoxib. Preferably, the parecoxib or salt thereof, for example the sodium salt, is administered in a daily dosage amount of about 1 mg to about 200 mg. More preferred daily dosage amounts are about 5 mg to about 120 mg, more preferably about 10 mg to about 100 mg, for example about 20 mg, about 40 mg or about 80 mg, parecoxib.

In an especially surprising finding, illustrated in FIG. 1, so rapid and complete is the conversion of parecoxib to valdecoxib that parenteral, for example intravenous, administration of parecoxib to a human subject provides a significantly earlier peak of blood plasma concentration of valdecoxib than does oral administration of valdecoxib itself at equal dose in immediate release form.

In a further embodiment of the invention, an article of manufacture is provided comprising a sealed vial, preferably a glass vial, containing a sterile parenterally deliverable composition that comprises parecoxib or a salt thereof in a parecoxib dosage amount equal to a therapeutically effective dosage of valdecoxib. Preferably the dosage amount of parecoxib is about 1 mg to about 200 mg, more preferably about 5 mg to about 120 mg, and most preferably about 10 mg to about 100 mg, for example about 20 mg, about 40 mg or about 80 mg. Preferably the parecoxib is present as parecoxib sodium. Optionally the vial is a multicompartment vial as hereinabove described.

Therapeutic methods of the present invention further include combination therapies of parecoxib or a composition of the invention with one or more drugs selected from opioids and other analgesics, including narcotic analgesics, Mu receptor antagonists, Kappa receptor antagonists, non-narcotic (i.e. non-addictive) analgesics, monoamine uptake inhibitors, adenosine regulating agents, cannabinoid derivatives, Substance P antagonists, neurokinin-1 receptor antagonists and sodium channel blockers, among others. Preferred combination therapies comprise use of a composition of the invention with one or more compounds selected from aceclofenac, acemetacin, e-acetamidocaproic acid, acetaminophen, acetaminosalol, acetanilide, acetylsalicylic acid (aspirin), S-adenosylmethionine, alclofenac, alfentanil, allylprodine, alminoprofen, aloxiprin, alphaprodine, aluminum bis(acetylsalicylate), amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antipyrine salicylate, antrafenine, apazone, bendazac, benorylate, benoxaprofen, benzpiperylon, benzydamine, benzylmorphine, bermoprofen, bezitramide, α-bisabolol, bromfenac, p-bromoacetanilide, 5-bromosalicylic acid acetate, bromosaligenin, bucetin, bucloxic acid, bucolome, bufexamac, bumadizon, buprenorphine, butacetin, butibufen, butophanol, calcium acetylsalicylate, carbamazepine, carbiphene, carprofen, carsalam, chlorobutanol, chlorthenoxazin, choline salicylate, cinchophen, cinmetacin, ciramadol, clidanac, clometacin, clonitazene, clonixin, clopirac, clove, codeine, codeine methyl bromide, codeine phosphate, codeine sulfate, cropropamide, crotethamide, desomorphine, dexoxadrol, dextromoramide, dezocine, diampromide, diclofenac sodium, difenamizole, difenpiramide, diflunisal, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, flufenamic acid, flunoxaprofen, fluoresone, flupirtine, fluproquazone, flurbiprofen, fosfosal, gentisic acid, glafenine, glucametacin, glycol salicylate, guaiazulene, hydrocodone, hydromorphone, hydroxypethidine, ibufenac, ibuprofen, ibuproxam, imidazole salicylate, indomethacin, indoprofen, isofezolac, isoladol, isomethadone, isonixin, isoxepac, isoxicam, ketobemidone, ketoprofen, ketorolac, p-lactophenetide, lefetamine, levorphanol, lofentanil, lonazolac, lornoxicam, loxoprofen, lysine acetylsalicylate, magnesium acetylsalicylate, meclofenamic acid, mefenamic acid, meperidine, meptazinol, mesalamine, metazocine, methadone hydrochloride, methotrimeprazine, metiazinic acid, metofoline, metopon, mofebutazone, mofezolac, morazone, morphine, morphine hydrochloride, morphine sulfate, morpholine salicylate, myrophine, nabumetone, nalbuphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paranyline, parsalmide, pentazocine, perisoxal, phenacetin, phenadoxone, phenazocine, phenazopyridine hydrochloride, phenocoll, phenoperidine, phenopyrazone, phenyl acetylsalicylate, phenylbutazone, phenyl salicylate, phenyramidol, piketoprofen, piminodine, pipebuzone, piperylone, piprofen, pirazolac, piritramide, piroxicam, pranoprofen, proglumetacin, proheptazine, promedol, propacetamol, propiram, propoxyphene, propyphenazone, proquazone, protizinic acid, ramifenazone, remifentanil, rimazolium metilsulfate, salacetamide, salicin, salicylamide, salicylamide o-acetic acid, salicylsulfuric acid, salsalte, salverine, simetride, sodium salicylate, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tolfenamic acid, tolmetin, tramadol, tropesin, viminol, xenbucin, ximoprofen, zaltoprofen and zomepirac (see *The Merck Index,* 12th Edition, Therapeutic Category and Biological Activity Index, ed. S. Budavari (1996), pp. Ther-2 to Ther-3 and Ther-12 (Analgesic (Dental), Analgesic (Narcotic), Analgesic (Non-narcotic), Anti-inflammatory (Nonsteroidal)).

Particularly preferred combination therapies comprise use of parecoxib or a composition of the invention with an opioid compound, more particularly where the opioid compound is codeine, meperidine, morphine or a derivative thereof.

The drug being used in combination therapy with parecoxib or a composition of the invention can be administered by any route, including parenterally, orally, topically, etc.

EXAMPLES

The following examples illustrate aspects of the present invention but are not to be construed as limitations.

Example 1

Reconstitutable powder compositions, herein identified as Formulations A-D, were prepared as described below, containing respectively 5, 10, 20 and 40 mg dosage amounts of parecoxib in the form of parecoxib sodium.

First, solutions for lyophilization were prepared having compositions as shown in Table 1. Solutions A-D for lyophilization correspond to Formulations A-D respectively.

TABLE 1

Composition of Solutions A-D for lyophilization

| Ingredient | A | B | C | D |
|---|---|---|---|---|
| parecoxib sodium (mg) | 5.30 | 10.59 | 21.18 | 42.36 |
| dibasic sodium phosphate heptahydrate (mg) | 0.67 | 1.34 | 2.68 | 5.36 |
| phosphoric acid, 1M | as required for pH adjustment | | | |
| sodium hydroxide, 1N | as required for pH adjustment | | | |
| water for injection USP, to make (ml) | 1 | 1 | 1 | 2 |

In preparation of each of the above solutions for lyophilization, dibasic sodium phosphate heptahydrate was dissolved in a suitable volume of water for injection and pH of the resulting solution was adjusted to 8.1 using 1M phosphoric acid. Parecoxib sodium was dissolved in this solution. The pH was checked and readjusted if necessary with 1M phosphoric acid or 1N sodium hydroxide and the volume was adjusted to a target volume by addition of water to form the solution for lyophilization. The volume of each solution prepared was sufficient to prepare several unit dosage compositions (1 ml or 2 ml of solution per unit dose as indicated in Table 1).

The solution for lyophilization was passed through two 0.2 μm Durapore® sterilizing filters and 1 ml or 2 ml of the solution was aseptically filled into 2 ml or 5 ml, Type I, untreated, depyrogenated, clear glass vials, respectively. The filling was metered by weight. Average density of several lots of each solution was 1.005 g/ml. In a separate test, parecoxib sodium was found not to bind to the sterilizing filters.

The vials were partially stoppered with sterilized lyophilization stoppers (having an opening to permit sublimation), and were placed in a previously sterilized lyophilization chamber and subjected to a lyophilization cycle. A typical cycle used is as described in Table 2. Sterile nitrogen was used to fill the headspace of the vials and to break the vacuum on completion of the cycle. The vials were fully stoppered while in the chamber. Upon removal from the chamber the vials were immediately sealed with flip-off aluminum seals crimped into place, and were then stored at room temperature, protected from light.

TABLE 2

Typical lyophilization cycle

| Phase | Description |
|---|---|
| freezing | room temperature to −50° C. in 1.75 h |
| | hold at −50° C. for 7.0 h |
| primary drying | −50° C. to 15° C. in 1.5 h |
| | hold at 15° C. for 2.25 h |
| | 15° C. to 45° C. in 1.0 h |
| | hold at 45° C. for 16.5 h |
| | vacuum 300 μm Hg |
| secondary drying | 45° C. to room temperature in 5.0 h |
| | vacuum 300 μm Hg |
| total cycle time | 36 h |

The resulting Formulations A-D formed cakes in the vials showing good appearance, i.e., with no cracking or collapsing of the cake. Powder X-ray diffraction (PXRD) analysis indicated that the cakes were amorphous. Even after storage at 70° C. for 12 weeks, PXRD analysis showed no change in physical character of the cakes, and no evidence of collapse was seen.

Formulations A, B and C (5, 10 and 20 mg parecoxib) were analyzed for residual water content and, as an indication of chemical stability, for valdecoxib. Valdecoxib analysis, by HPLC, was performed on freshly prepared samples and on samples stored for 12 weeks at 70° C. Data, shown in Table 3, show excellent chemical stability, with less than 0.5% valdecoxib even after 12 weeks high temperature storage.

TABLE 3

Stability of Formulations A-C

| Parameter | A | B | C |
|---|---|---|---|
| water (%), fresh sample | 1.6 | 1.4 | 0.8 |
| valdecoxib (%), fresh sample | 0.06 | 0.07 | 0.03 |
| valdecoxib (%), stored 12 weeks at 70° C. | 0.45 | 0.37 | 0.36 |

Formulation D (40 mg parecoxib) was tested for pH and residual water content and analyzed for parecoxib and valdecoxib by HPLC when freshly prepared and following 4, 8 and 12 weeks storage at various temperatures. Data, shown in Table 4, show excellent chemical stability, with less than 0.5% valdecoxib even after 12 weeks high temperature storage. Parecoxib and valdecoxib percentages are expressed on an excipient-free basis.

TABLE 4

Stability of Formulation D

| Storage temperature and time of sampling | parecoxib % | valdecoxib % | water % | pH |
|---|---|---|---|---|
| freshly prepared | 97.4 | 0.03 | 1.00 | 7.9 |
| 40° C., 4 weeks | 97.1 | 0.03 | 1.06 | 8.0 |
| 40° C., 8 weeks | 96.4 | 0.03 | 1.08 | 7.8 |
| 40° C., 12 weeks | 96.9 | 0.04 | 1.29 | 7.8 |
| 55° C., 4 weeks | 96.8 | 0.05 | 1.03 | 8.0 |
| 55° C., 8 weeks | 96.8 | 0.07 | 0.84 | 7.8 |
| 55° C., 12 weeks | 95.4 | 0.09 | 0.87 | 7.9 |
| 70° C., 4 weeks | 97.3 | 0.14 | 0.90 | 8.0 |
| 70° C., 8 weeks | 96.6 | 0.20 | 0.77 | 7.8 |
| 70° C., 12 weeks | no data | 0.36 | no data | no data |

Formulations A-C were reconstituted in 1 ml, and Formulation D in 2 ml, 0.9% sodium chloride injection USP. The cakes dissolved instantaneously.

Example 2

Reconstitutable powder compositions, herein identified as Formulations E-J, were prepared as described below, each containing 20 mg parecoxib in the form of parecoxib sodium. Solutions for lyophilization were first prepared having compositions as shown in Table 5. Solutions E-J for lyophilization correspond to Formulations E-J respectively. Preparation of the solutions and of the lyophilized powder compositions was by a procedure similar to that for Formulations A-D in Example 1.

It will be noted that each of Formulations E-J contains more than about 10% of excipient ingredients other than the buffering agent (dibasic sodium phosphate or tromethamine). These formulations are presented here for comparative purposes.

TABLE 5

Composition of Solutions E-J for lyophilization

| Ingredient | E | F | G | H | I | J |
|---|---|---|---|---|---|---|
| parecoxib sodium (mg) | 21.18 | 21.18 | 21.18 | 21.18 | 21.18 | 21.18 |
| dibasic sodium phosphate heptahydrate (mg) | | 2.68 | | 2.68 | 2.68 | 2.68 |
| tromethamine (mg) | 1.2 | | 1.2 | | | |
| mannitol (mg) | 30 | 30 | | | 30 | 30 |
| glycine (mg) | | | 13.5 | 13.5 | | |
| polyethylene glycol 4000 (mg) | | | | | 200 | |
| sulfobutyl-β-cyclodextrin (mg) | | | | | | 15 |
| hydrochloric acid, 1N | as required for pH adjustment | | | | | |
| sodium hydroxide, 1N | as required for pH adjustment | | | | | |
| water for injection USP, to make (ml) | 1 | 1 | 1 | 1 | 1 | 1 |

Formulations E-J were analyzed for parecoxib and valdecoxib, when freshly prepared and after 4 weeks storage at various temperatures. Parecoxib and valdecoxib percentages are expressed in Table 6 on an excipient-free basis.

TABLE 6

Stability of Formulations E-J

| Parameter | E | F | G | H | I | J |
|---|---|---|---|---|---|---|
| parecoxib (%), as prepared | 99.00 | 99.40 | 104.3 | 102.2 | 90.46 | 99.86 |
| parecoxib (%), 5° C., 4 weeks | 95.71 | 95.76 | 100.0 | 98.04 | 90.17 | 98.76 |
| parecoxib (%), 55° C., 4 weeks | 98.79 | 99.00 | 98.37 | 98.03 | 87.57 | 97.41 |
| parecoxib (%), 70° C., 4 weeks | 87.60 | 98.00 | 82.77 | 92.81 | 85.58 | 90.00 |
| valdecoxib (%), as prepared | 0.19 | 0.17 | 0.25 | 0.26 | 0.16 | 0.20 |
| valdecoxib (%), 5° C., 4 weeks | 0.20 | 0.12 | 0.19 | 0.19 | 0.13 | 0.14 |
| valdecoxib (%), 55° C., 4 weeks | 1.43 | 0.26 | 1.72 | 1.38 | 0.43 | 1.04 |
| valdecoxib (%), 70° C., 4 weeks | 9.03 | 0.89 | 15.08 | 5.26 | 0.95 | 8.81 |

It will be noted that Formulations E-J exhibited poorer chemical stability than Formulations A-D of the invention. Formulations F and I, each of which contained 30 mg mannitol in addition to dibasic sodium phosphate, exhibited the greatest stability of the formulations tested in this Example, but nonetheless showed a much greater degree of conversion of parecoxib to valdecoxib than did Formulations A-D after storage for 4 weeks at 55° C. or 70° C. Chemical stability of Formulations E, G, H and J was unacceptably poor.

Furthermore, none of formulations E-J exhibited instantaneous dissolution upon reconstitution. Formulation I, which contained 200 mg polyethylene glycol 4000 in addition to mannitol and dibasic sodium phosphate, proved especially slow and difficult to dissolve in attempts to reconstitute the formulation.

Example 3

Blood plasma concentration of valdecoxib in human subjects was determined in a pharmacokinetic study. In 11 healthy adult subjects, a single intravenous (IV) 20 mg dose of parecoxib, as parecoxib sodium, was administered in a 1 ml bolus, or a single 20 mg dose of valdecoxib was administered orally in the form of an immediate-release tablet, with 240 ml water. Subjects drank 180 ml water one, two and three hours postdose.

Valdecoxib blood plasma concentration was determined using a validated high performance liquid chromatography (HPLC) procedure. The mean plasma concentration of valdecoxib from 0 to 24 hours postdose is shown in FIG. 1.

Maximum blood plasma concentration of valdecoxib was reached earlier when parecoxib sodium was administered intravenously than when valdecoxib was administered orally.

Example 4

In a single-center, single-dose, randomized, double-blind, placebo-controlled, parallel group 24-hour study, a group of 224 patients (56 in each treatment group) requiring extraction of two ipsilateral impacted third molars including bony resection, men and women 18-45 years of age inclusive, were randomized to receive a single preemptive intravenous dose of 20 mg, 40 mg or 80 mg parecoxib, or placebo, in 4 ml volume of 0.9% sodium chloride.

Beginning at 30 minutes after closure of surgery, level of pain was assessed every two hours up to 24 hours, except that patients were not awakened for pain assessments. Pain was assessed by the patient on a 0-3 scale and on a chart representing a continuum from "no pain" to "worst pain". Rescue medication was administered on demand by the patient. At the last scheduled assessment, or immediately prior to administration of rescue medication, the patient was asked to evaluate the effectiveness of the study medication to delay pain.

Time to rescue medication (TRM) was analyzed using survival analysis techniques. The median time to event for each treatment group was calculated using the Kaplan-Meier product limit estimator, including the adjustment described by Miller (1981) in *Survival Analysis*, pp. 74-75. New York: John Wiley & Sons. Ninety five percent (95%) confidence intervals for the median time to event were calculated using the method of Simon & Lee (1982), *Cancer Treat. Rep.* 66, 37-42. For TRM, patients who did not require rescue medication up to the 24 hour assessment were considered censored at 24 hours. Patients who dropped out for reasons other than administration of rescue medication were censored at the time they dropped out of the study.

On the basis of median TRM (Table 7), single doses of parecoxib 20 mg, 40 mg and 80 mg resulted in significantly longer TRM than placebo. Median TRM values for parecoxib 40 mg and 80 mg were not significantly different from one another, but both were significantly longer than TRM for parecoxib 20 mg.

The proportion of patients taking rescue medication (also shown in Table 7) was significantly lower for the parecoxib treatment groups than in the placebo treatment group; there was no significant difference between the parecoxib 40 mg and 80 mg treatment groups with respect to this parameter.

TABLE 7

Time to rescue medication (TRM)

| Treatment group | Median TRM | 95% confidence interval | Patients taking rescue medication |
|---|---|---|---|
| Placebo | 2 h 51 m | 2 h 16 m to 3 h 16 m | 93% |
| Parecoxib 20 mg | 6 h 17 m | 4 h 04 m to 11 h 17 m | 78% |
| Parecoxib 40 mg | >24 h | 11 h 04 m to >24 h | 48% |
| Parecoxib 80 mg | 12 h 00 m | 6 h 24 m to 16 h 37 m | 59% |

With respect to the patient's evaluation of effectiveness of the study medication, scores for patients in each of the parecoxib treatment groups were significantly higher than those in the placebo treatment group; there were no significant differences between the parecoxib 40 mg and 80 mg treatment groups. Of the patients in the parecoxib 40 mg treatment group, 92% rated the study medication as "good" or "excellent".

What is claimed is:

1. A pharmaceutical composition comprising, in powder form:
   (a) parecoxib, or a salt thereof, in a therapeutically effective total amount constituting about 30% to about 90% by weight of the composition;
   (b) a parenterally acceptable buffering agent in an amount of about 10% to about 60% by weight of the composition; and
   (c) said parecoxib and buffering agent present in an amount from about 90% to about 100% by weight of the composition
said composition being reconstitutable in a parenterally acceptable solvent liquid to form an injectable solution.

2. The composition of claim 1 wherein the parecoxib or salt thereof is parecoxib sodium.

3. The composition of claim 1 wherein the parecoxib of salt thereof is presented in an amount of about 40% to about 85% by weight of the composition.

4. The composition of claim 1 wherein the parecoxib of salt thereof is present in an amount of about 50 to about 80% by weight of the composition.

5. The composition of claim 1 wherein the buffering agent is present in an amount of about 20% to about 50% by weight of the composition.

6. The composition of claim 1 that consists of the parecoxib or salt thereof and the buffering agent.

7. The composition of claim 1 wherein the buffering agent is selected from the group consisting of:
   sodium and potassium phosphates, sodium and potassium citrates, mono-, di- and trethanolamines, tromethamine; and mixtures thereof.

8. The composition of claim 1 wherein the buffering agent is selected from the group consisting of:
   Dibasic sodium and potassium phosphates, dibasic phosphate; and mixtures thereof.

9. The composition of claim 1 wherein the buffering agent is dibasic sodium phosphate.

10. The composition of claim 1 that, upon reconstitution, has a pH of about 7 to about 9.

11. The composition of claim 1 having sufficient porosity to permit rapid dissolution of the parecoxib, or salt thereof, upon reconstitution.

12. An injectable solution prepared by reconstituting a powder comprising:
   (a) parecoxib, or a salt thereof, in a therapeutically effective total amount constituting about 30% ro about 90% by weight of the powder;
   (b) a parenterally acceptable buffering agent in an amount of about 10% to about 60% by weight of the powder; and
   (c) wherein said parecoxib and buffering agent are present in an amount from about 90% to about 100% by weight of the powder, in a parenterally acceptable solvent.

13. The solution of claim 12 wherein the solvent is an aqueous solvent.

14. The solution of claim 12 having a pH of about 7.5 to about 8.5.

15. The solution of claim 13 wherein the aqueous solvent contains dextrose or sodium chloride or both.

16. An injectable solution prepared by reconstituting powder comprising:
   (a) parecoxib sodium in a therapeutically effective total amount constituting about 30% ro about 90% by weight of the powder;
   (b) a parenterally acceptable buffering agent in an amount of about 10% to about 60% by weight of the powder; and
   (c) wherein said parecoxib and buffering agent are present in an amount from about 90% to about 100% by weight of the powder, in a parenterally acceptable solvent.

17. The solution of claim 16 wherein the solvent is an aqueous solvent.

18. The solution of claim 17 having a pH of about 7.5 to about 8.5.

19. The solution of claim 17 wherein the aqueous solvent contains dextrose or sodium chloride or both.

20. An article of manufacture comprising a sealed vial having contained therewithin a unit dosage amount of a composition of claim 1 in a sterile condition.

21. The article of manufacture of claim 20 wherein the vial is a multicompartment vial.

22. An article of manufacture comprising a sealed vial having contained therewithin a unit dosage amount of a composition of claim 2 in a sterile condition.

23. The article of manufacture of claim 22 wherein the parecoxib sodium is present in a parecoxib dosage amount of about 1 mg to about 200 mg.

24. The article of manufacture of claim 22 wherein the parecoxib sodium is present in a parecoxib dosage amount of 5 mg to about 120 mg.

25. The article of manufacture of claim 22 wherein the parecoxib sodium is present in a parecoxib dosage amount of about 10 mg to about 100 mg.

26. The article of manufacture of claim 22 wherein the vial is a multicompartment vial.

27. A process for preparing a reconstitutable selective COX-2 inhibitory composition, the process comprising a step of lyophilizing an aqueous solution that comprises:
   (a) parecoxib, or a salt thereof, in a therapeutically effective total amount constituting about 30% to about 90% by weight of the composition, excluding water;
   (b) a parenterally acceptable buffering agent in an amount of about 10% to about 60% by weight of the composition, excluding water; and
   (c) wherein said parecoxib and said buffering agent are present in an amount from about 90% to about 100% by weight, excluding water;

said lyophilizing step resulting in the formation of a readily reconstitutable powder; and said composition being reconstitutable in a parenterally acceptable solvent liquid to form an injectable solution.

28. The process of claim 27 wherein the parecoxib or salt thereof is parecoxib sodium.

29. The process of claim 28 wherein the buffering agent is dibasic sodium phosphate.

30. The process of claim 29 wherein, prior to the lyophilizing step, the solution is prepared by dissolving the parecoxib sodium and the dibasic sodium phosphate in water for injection, sterilized and the metered into vials, each containing a volume of solution having a unit dosage amount of parecoxib sodium, and the vials are placed in a lyophilization chamber.

31. The process of claim 30 wherein, in the step of preparing the solution, the parecoxib sodium is added last.

32. The process of claim 29 wherein the lyophilizing step comprises a freezing phase, a primary drying phase and a secondary drying phase.

33. The process of claim 32 wherein:
(a) in the freezing phase, temperature is lowered to a freezing temperature of about $-30°$ C. to about $-60°$ C./over a period of about 1 to about 5 hours and is held at the freezing temperature for about 0.5 to about 24 hours;
(b) in the primary drying phase, a vacuum of about 25 to about 500 μm Hg is drawn, and temperature is raised from the freezing temperature to about $0°$ C. over a period of about 1 to about 5 hours; and
(c) in the secondary drying phase, under vacuum of about 25 to about 500 μm Hg. Temperature is raised from about $0°$ C. to a level above room temperature over a period of about 1 to about 4 hours and is held at the raised level for about 3 to about 12 hours; to result in a powder having a moisture content of less than about 2% by weight.

34. The process of claim 32 wherein overall lyophilization cycle time is about 18 to about 24 hours.

* * * * *